(12) United States Patent
Ovokaitys et al.

(10) Patent No.: US 8,377,989 B2
(45) Date of Patent: Feb. 19, 2013

(54) ROOM TEMPERATURE STABLE NON-CRYSTALLINE ASPIRIN AND METHOD FOR THE PREPARATION THEREOF

(75) Inventors: Todd F. Ovokaitys, Carlsbad, CA (US); John Scott Strachan, Edinburgh (GB)

(73) Assignee: Todd F. Ovokaitys, Carlsbad, CA (US)

( * ) Notice: Subject to any disclaimer, the term of this patent is extended or adjusted under 35 U.S.C. 154(b) by 591 days.

(21) Appl. No.: 12/252,447

(22) Filed: Oct. 16, 2008

(65) Prior Publication Data
US 2009/0131710 A1    May 21, 2009

Related U.S. Application Data

(60) Provisional application No. 60/999,445, filed on Oct. 17, 2007, provisional application No. 60/999,462, filed on Oct. 17, 2007, provisional application No. 60/999,483, filed on Oct. 17, 2007.

(51) Int. Cl.
*A61K 31/235* (2006.01)
*C07C 69/017* (2006.01)

(52) U.S. Cl. ........................ 514/548; 560/143
(58) Field of Classification Search ............... None
See application file for complete search history.

(56) References Cited

U.S. PATENT DOCUMENTS

| | | | |
|---|---|---|---|
| 3,703,576 A * | 11/1972 | Kitajima et al. | 424/495 |
| 6,064,500 A | 5/2000 | Strachan | |
| 6,811,564 B1 | 11/2004 | Strachan | |
| 2004/0247671 A1 | 12/2004 | Prescott et al. | |
| 2005/0188921 A1 | 9/2005 | Malone | |
| 2006/0013869 A1 | 1/2006 | Ignatious et al. | |

FOREIGN PATENT DOCUMENTS

| | | |
|---|---|---|
| RU | 2099059 | 12/1997 |
| WO | 01/00563 | 1/2001 |

OTHER PUBLICATIONS

Rouhi, Chemical and Engineering News, The Right Stuff, 2003, 81(8), pp. 32-35.*
Konno et al, Chemical and Pharmaceutical Bulletin, Physical and Chemical Changes of Medicinals in Mixtures with Adsorbents in the Solid State. I. Effect of Vapor Pressure of the Medicinals on Changes in Crystalline Properties, 1986, 34(1), pp. 301-307.*
Pajula et al, (Molecular Pharmaceutics, Predicting the Formation and Stability of Amorphous Small Molecule Binary Mixtures from Computationally Determined Flory-Huggins Interaction Parameter and Phase Diagram, 2010, 7(3), pp. 795-804.*
International Search Report and Written Opinion dated Dec. 15, 2008 for PCT/US08/80098.
Johari et al., *Physical Chemistry Chemical Physics*, 2000, 2, 5479-5484.
Zaworotko et al., J. Am. Chem. Soc. 2005, *Chemical & Engineering News*, 127, 16802, Nov. 21, 2005.
Duddu, S.P. et al., "Importance of glass transition temperature in accelerated stability testing of amorphous solids: case study using a lyomphilized aspirin formulation", Journal of Pharmaceutical Sciences, American Pharmaceutical Association, Washington, US, vol. 85, No. 3, Mar. 1, 1996, pp. 345-347.
Extended European Search Report of European Patent Application 08840270.6, dated Aug. 2, 2011.
Eurasian Search Report, dated Jun. 14, 2011.

* cited by examiner

*Primary Examiner* — Paul A Zucker
(74) *Attorney, Agent, or Firm* — Kenyon & Kenyon LLP

(57) ABSTRACT

The present invention provides stable non-crystalline aspirin that does not crystallize at room temperature during storage for prolonged periods of time and processes for obtaining the stable non-crystalline aspirin.

33 Claims, 6 Drawing Sheets

ROOM TEMPERATURE STABLE NON-CRYSTALLINE ASPIRIN AND METHOD FOR THE PREPARATION THEREOF

RELATED APPLICATIONS

This application claims benefit of U.S. Provisional Patent Applications Nos. 60/999,445, 60/999,462, and 60/999,483, all filed Oct. 17, 2007, the contents of which are incorporated herein in their entirety by reference. This application is also related to U.S. patent application Ser. No. 12/252,458, titled PROCESS FOR THE MODIFICATION OF THE SOLID STATE OF A COMPOUND AND CO-AMORPHOUS COMPOSITIONS PRODUCED WITH SAME, filed on even date herewith, the contents of which are also incorporated herein in their entirety.

FIELD OF THE INVENTION

The present invention is directed to non-crystalline glass aspirin that is stable at room temperature and to processes for its preparation.

BACKGROUND

Acetylsalicylic acid (ASA) was first synthesized by Charles Gerhardt in 1853. However, Gerhardt did not pursue his invention. Bayer commercialized crystalline acetylsalicylic acid in 1899 under the trade name ASPIRIN. U.S. Pat. No. 644,077 for the crystalline acetylsalicylic acid was granted in 1900 to Felix Hoffmann, a Bayer chemist. Until recently, the original crystalline form, known as Form I, was the only known crystalline form of aspirin and the only form of aspirin that is stable at room temperature. As reported in *Chemical & Engineering News*, Nov. 21, 2005, Zaworotko et al., *J. Am. Chem. Soc.*, 2005, 127, 16802, reported the synthesis of a second polymorphic form of aspirin. Aspirin Form II is kinetically stable at 100 K (−173° C.), but converts back to Form I at ambient conditions Amorphous glass aspirin has also been formed. However, except possibly for some microscopic residues, amorphous aspirin has been produced only at very low temperatures. Above the glass transition temperature of about 243 Kelvin (−30° C.), amorphous aspirin converts rapidly to the crystalline Form I. Thus, all prior art forms of aspirin convert to Form I at room temperature. As a result of the low temperature required to create and maintain the amorphous form, there has been essentially no practical application of the amorphous solid state form.

Johari et al., *Physical Chemistry Chemical Physics*, 2000, 2, 5479-5484, report the vitrification of aspirin by melting and cooling and by ball-milling at ambient temperature to form a vitreous or supercooled viscous liquid aspirin that is stable against crystallization for several days at 298K. The viscous liquid was found to flow slowly when tilted in a container, but did not crystallize for four to five days at 298K. The vitreous aspirin samples did ultimately undergo complete crystallization, which was accelerated when the samples were kept at about 340K.

Johari et al. report that the vitreous state has a higher energy state than the crystal state with a lower frequency of its phonon modes and a greater anharmonicity that make absorption and assimilation directly from the solid state more effective and efficient. In its bulk form, the vitreous aspirin is reported to dissolve more slowly than the same mass of finely powdered crystals of aspirin. As is well known in the art, a bulk sample of a substance has a significantly smaller surface area than finely powdered crystals. That makes the dissolution of the bulk form much more difficult, accounting for the slower dissolution rate of the bulk vitreous aspirin reported by Johari et al.

SUMMARY OF THE INVENTION

The present invention is directed to non-crystalline aspirin. Non-crystalline aspirin in accordance with the invention does not crystallize during storage for at least about 30 days, preferably, for at least six months, and more preferably for at least about one year at a temperature of from about 20° to about 30° C. The non-crystalline aspirin of the invention may be microencapsulated.

The present invention is also directed to a process for the preparation of non-crystalline aspirin. The process comprises applying laser radiation from at least two different lasers to a solution of aspirin in a solvent, and evaporating the solvent. Preferably, the laser radiation has pulses with an effective average pulse length of no more than about $10^{-9}$ seconds, and the laser radiation from each laser has a different wavelength. Preferably, at least one of the lasers emits visible light. More preferably, one laser emits radiation in the near UV to blue range, and one laser emits radiation in the red to near IR range. Good results have been obtained with laser radiation from one laser that emits radiation having a wavelength in the range of from about 400 to about 470 nm, and one laser that emits radiation having a wavelength in the range of from about 620 to about 680 nm.

Preferably, the laser radiation is modified with a Strachan Device, i.e., a device of the type disclosed by Strachan in U.S. Pat. Nos. 6,064,500 and 6,811,564. More preferably, the modified laser emissions are the emissions of lasers modified with the Strachan Device. Preferably, a Strachan Device enables the production of laser pulses having an effective average pulse length of less than about $10^{-12}$ seconds, and, preferably, no more than about $10^{-15}$ seconds. However, the Strachan Device interference pattern reduces the need for short pulses. The pulses of laser radiation from two lasers may be applied simultaneously or in alternating sequences.

Preferably, the solvent used in the aspirin solution is an alcohol, and, more preferably, is an absolute alcohol, such as absolute ethanol.

Preferably, in the process of the invention a solution of aspirin in a solvent is placed in a covered container, pulses of laser radiation pulses are applied to the to the aspirin solution, and at least a portion of the solvent is evaporated while applying the laser pulses, thereby forming non-crystalline aspirin. Preferably, the aspirin solution is heated during the application of the laser pulses. The laser radiation is preferably applied to the aspirin solution until the evaporation of the solvent is completed. The aspirin may be cooled to room temperature as the solvent evaporates.

Preferably, evaporation of solvent is prevented for a period of time after the application of laser pulses is initiated. The solvent is then evaporated while the application of laser pulses is continued.

Preferably, the non-crystalline aspirin of the invention is prepared in a process comprising: passing laser radiation through a Strachan Device, where the Strachan Device comprises a first diffraction grating and a second diffraction grating and a refractive element positioned between the first and second diffraction gratings. That cancels a portion of the laser radiation by destructive interference, and produces pulses of laser radiation by constructive interference. The laser radiation passed through the Strachan Device is then applied to a solution of aspirin in a solvent, and the solvent is evaporated, producing the non-crystalline aspirin of the invention. Preferably, after passing through the Strachan Device, the pulses of laser radiation have an effective average pulse length of no more than about $10^{-9}$ seconds.

DETAILED DESCRIPTION OF THE INVENTION

As used herein, the term "non-crystalline aspirin" refers to any form of aspirin that, upon a powder X-ray diffraction (PXRD) analysis, provides a PXRD pattern that is substantially free of any PXRD peaks that are typical of a PXRD pattern for crystalline aspirin.

The present invention is directed to a non-crystalline form of acetylsalicylic acid or aspirin that is stable at room temperature and to processes for producing the stable non-crystalline form of aspirin. The non-crystalline aspirin of the invention is stable at a temperature of about 20° to 30° C. for at least about 24 hours, preferably, for at least about 30 days, more preferably, for at least three months, and, most preferably, for at least about six months. Samples of the non-crystalline aspirin of the invention have remained stable at a temperature of about 20° to 30° C. for at least about a year.

Without being bound by theory, it is believed that the non-crystalline form of a compound has a higher free energy in the intermolecular lattice than any of the crystallized forms of the compound. This imparts a higher solubility in water to the non-crystalline form that can be about 2 to 8 times higher than that of the crystal form, where the non-crystalline and crystal forms have similar particle sizes. Such an increase in solubility can translate to faster dissolution, absorption, and clinical action, as well as significantly higher bioavailability. Thus, the non-crystalline aspirin of the invention provides a more rapid dissolution rate than crystalline aspirin under conditions following oral ingestion or trans-mucosal delivery, such as sublingual, and provides a higher solubility and bioavailability. Accordingly, the non-crystalline aspirin of the invention, which is stable at a temperature of from about 20° to about 30° C., should have clinical and other advantages over the crystalline form.

A powder X-ray diffraction (PXRD) analysis of crystalline aspirin and the non-crystalline aspirin of the invention demonstrates the difference in the arrangement of molecules in the two forms. A crystalline form of a compound has a PXRD pattern with characteristic peaks at particular reflection angles of the X-ray beam, measured in degrees 2θ. Typically, the resolution of a measurement is on the order of ±0.2° 2θ. The reflections are the result of the regular arrangement of the molecules in the crystal. In contrast, a partially non-crystalline sample of a compound has a PXRD pattern with substantially blunted or reduced peaks, and a sample of a purely non-crystalline compound has a PXRD pattern that is typically free of any characteristic peaks. The molecules are arranged randomly in a non-crystalline compound, and, thus, the reflection peaks are not observed in the PXRD pattern. Changes in intensity that occur over broad ranges may be observed in some non-crystalline compounds along with baseline noise.

Figure 1:
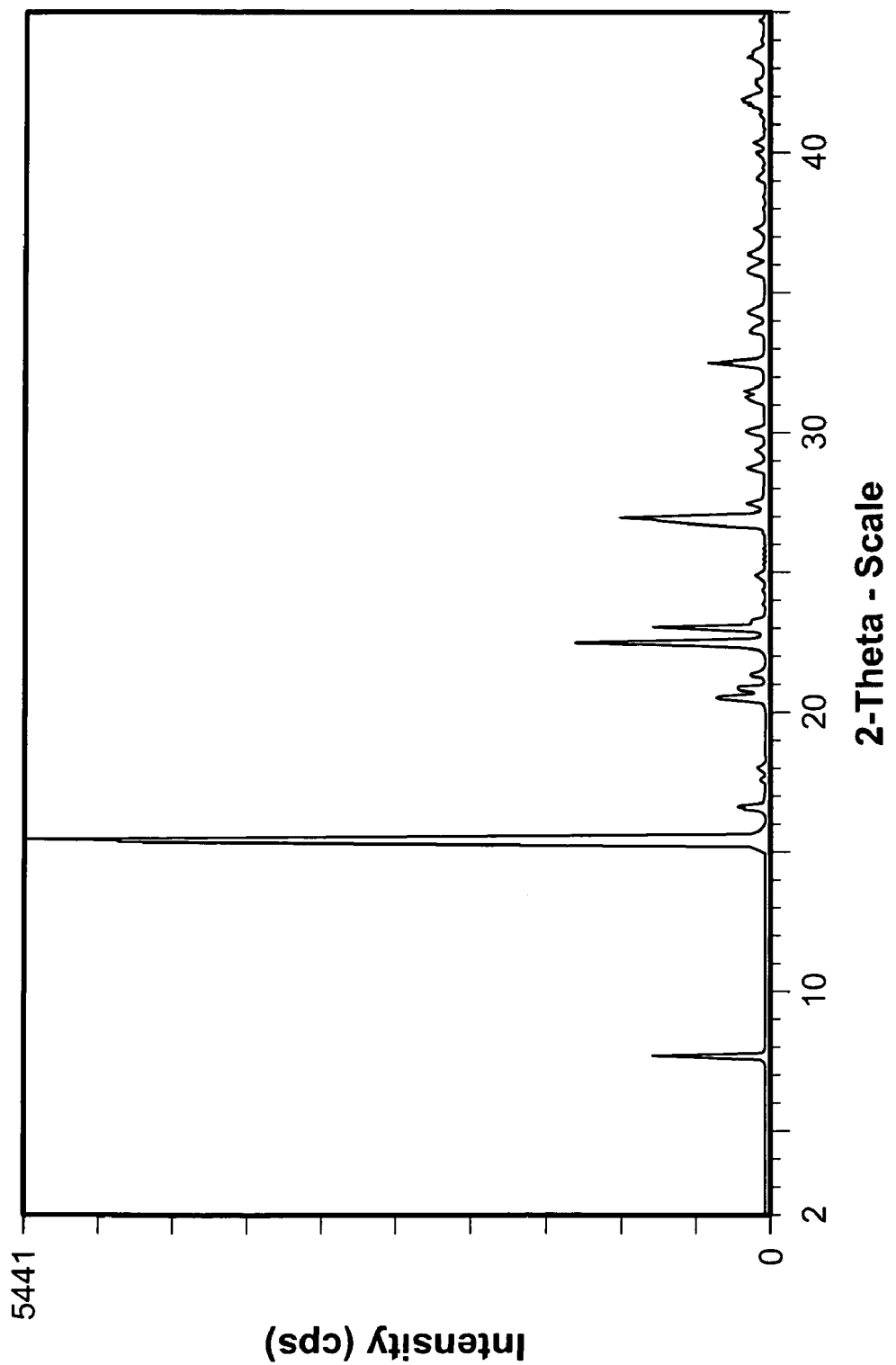
FIG. 1 illustrates the powder X-ray diffraction (PXRD) pattern of a control crystalline aspirin sample.

A typical PXRD pattern for crystalline aspirin is illustrated in FIG. 1. The PXRD pattern of FIG. 1 has a number of peaks, characteristic of crystalline aspirin.

Figure 2:
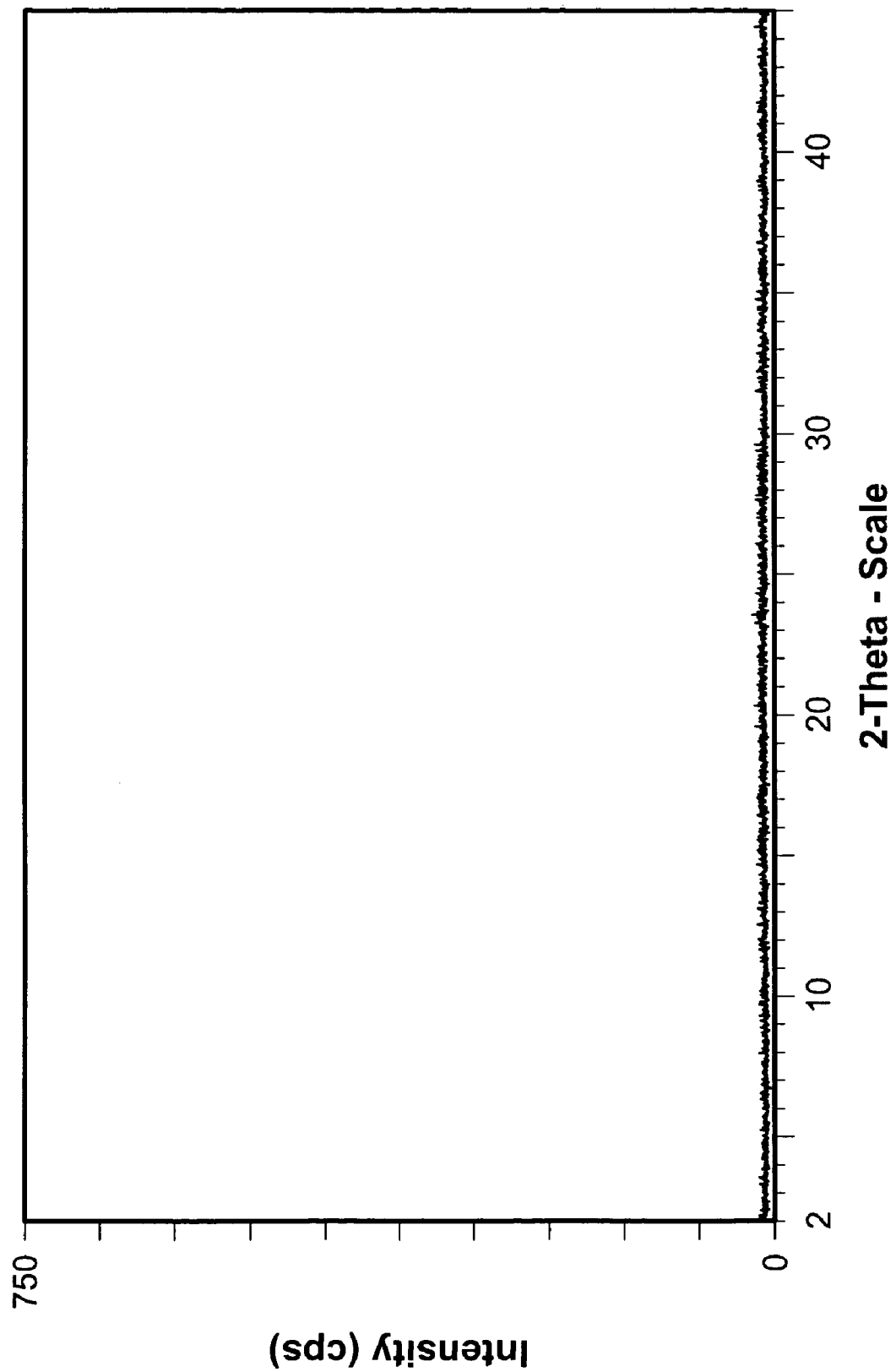
FIG. 2 illustrates the powder X-ray diffraction (PXRD) pattern of non-crystalline aspirin of the invention.

In contrast, FIG. 2 provides the PXRD pattern of non-crystalline aspirin of the invention. The PXRD pattern of the non-crystalline aspirin is in marked contrast to the highly crystalline pattern shown in FIG. 1 for the crystalline aspirin. The high intensity PXRD peaks of the crystalline aspirin are substantially absent, indicating that, at most, only very short range ordering is present in the non-crystalline aspirin of the invention. It is important to note that the resolution of the PXRD pattern of FIG. 1 is more than seven times greater than the resolution of the pattern illustrated in FIG. 2. Therefore, any of the peaks observed in the PXRD pattern of the crystalline aspirin in FIG. 1 that may be present in the PXRD pattern of the non-crystalline aspirin in FIG. 2 effectively have intensities no greater than the baseline noise in FIG. 1. This is clear evidence that the aspirin analyzed by PXRD, as illustrated in FIG. 2, is substantially pure non-crystalline aspirin. Ordering of the aspirin molecules in the sample that would result in PXRD peaks is substantially absent.

Given the strong thermodynamic tendency of aspirin to crystallize at room temperature, very short range microcrystalline formations may be present in the sample illustrated in FIG. 2. However, the PXRD pattern for non-crystalline aspirin at room temperature suggests that, at most, microcrystalline structures, having very short range ordering of not more than a few aspirin molecules, may be scattered randomly throughout the sample. Substantially the entire sample is made up of a continuous phase of complete randomization typical of a true glass that may contain a few, random microcrystalline structures, having very short range ordering. The physical and chemical properties of the non-crystalline aspirin of the invention are believed to be substantially the same as those that would be expected of a pure glass. The arrangement of molecules is substantially random, likely malting the non-crystalline aspirin more soluble than the crystalline form.

As with the disappearance of the characteristic reflection peaks of a PXRD pattern, as the amount of the non-crystalline form of a compound increases in a sample, the Fourier Transform Infrared (FTIR) spectroscopy absorption bands are broadened. This provides additional evidence of the presence of the non-crystalline form. Infrared spectra of crystalline materials typically exhibit sharper or better resolved absorption bands than the non-crystalline form. Some bands in an infrared spectrum may also be shifted somewhat because of changes in form between crystalline materials and the non-crystalline form of the same compound.

Figure 3:
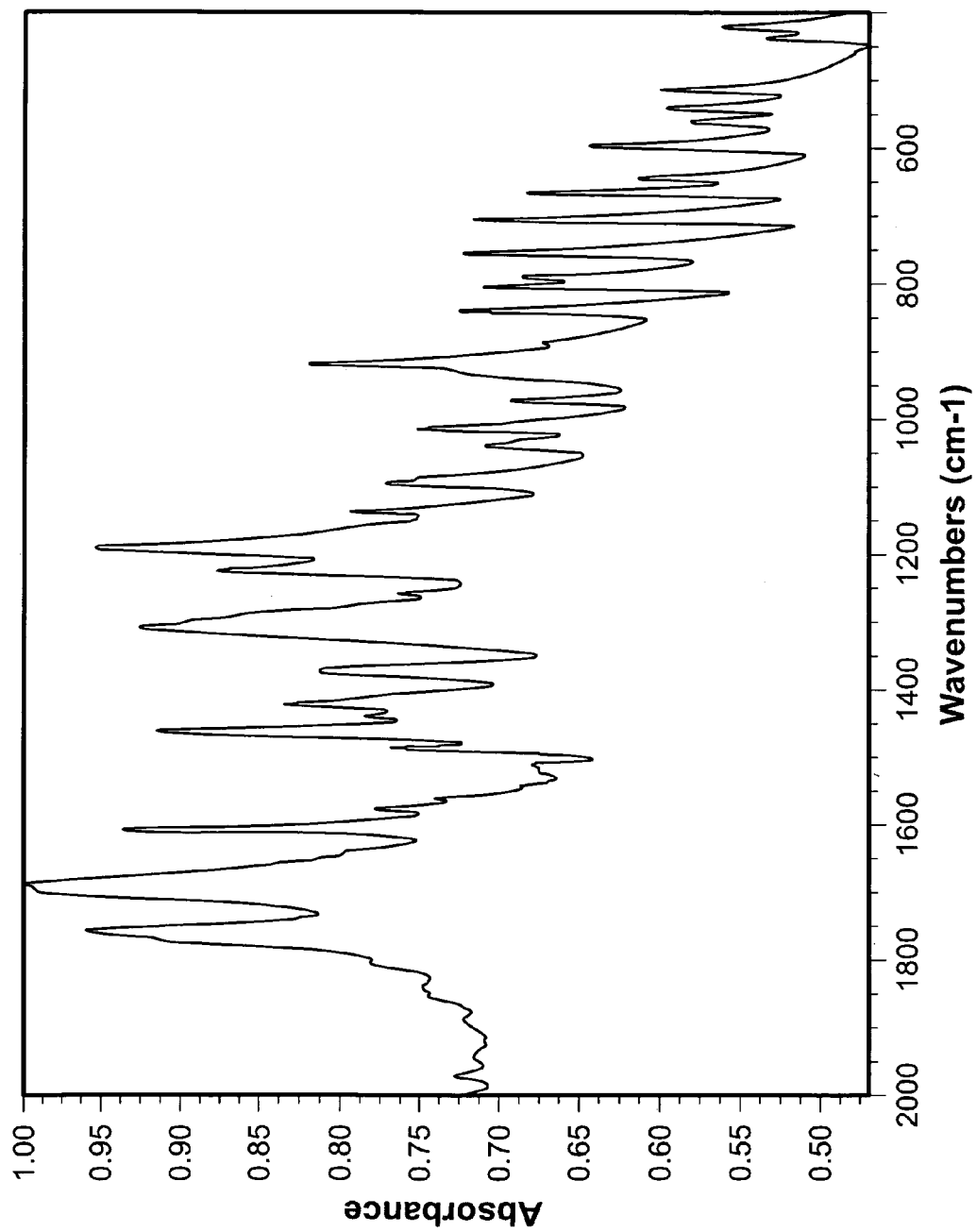
FIG. 3 illustrates an infrared spectroscopic pattern of the control crystalline aspirin sample.
Figure 4:
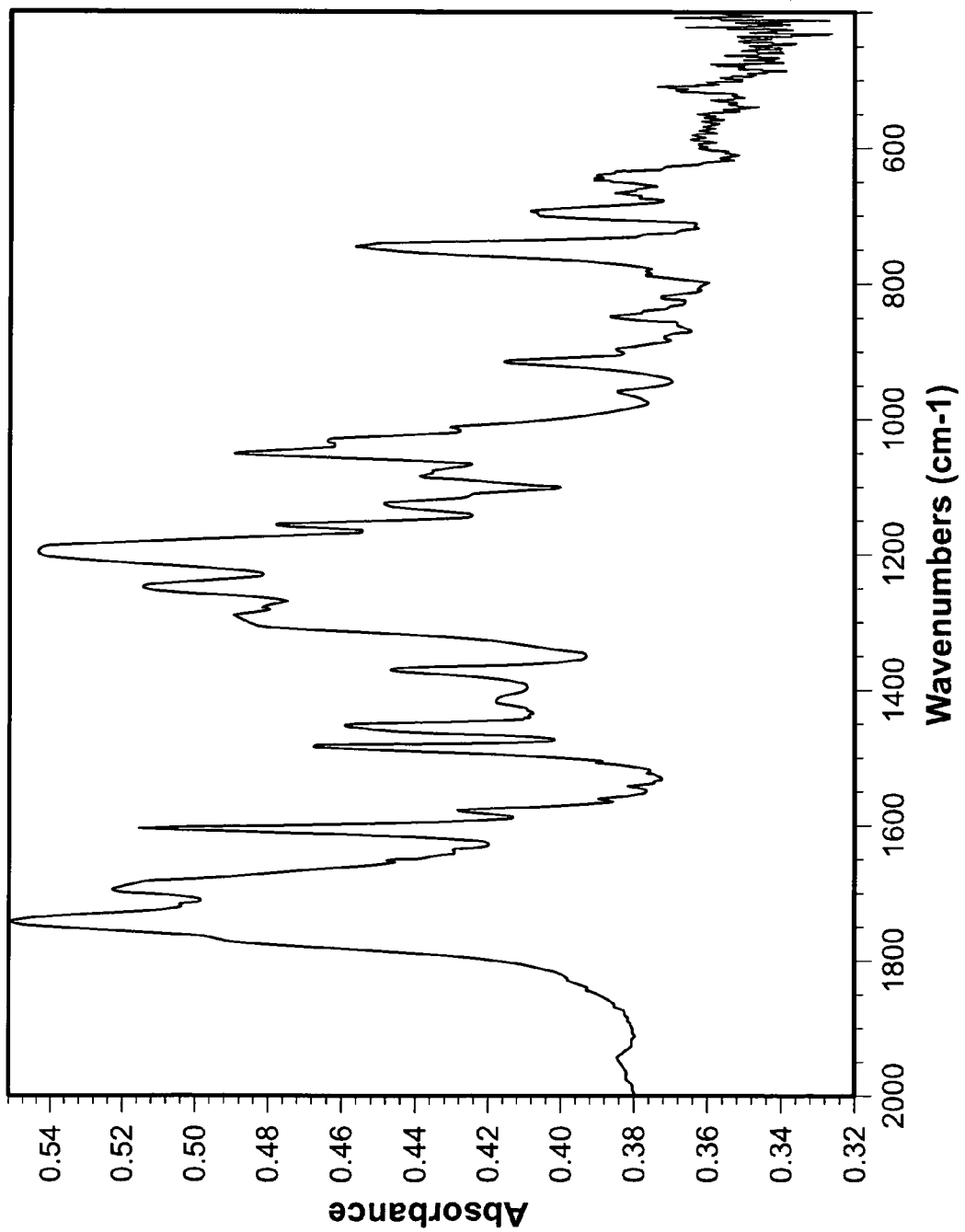
FIG. 4 illustrates the infrared spectroscopic pattern of non-crystalline aspirin of the invention, showing broadened absorption bands relative to the reference crystalline aspirin sample.

The results of FTIR analyses of crystalline and non-crystalline aspirin are illustrated in FIGS. 3 and 4, respectively. The aspirin samples are those analyzed by PXRD in FIGS. 1 and 2. The absorption peaks of the FTIR pattern of the crystalline aspirin, illustrated in FIG. 3 are relatively well defined. In contrast, the FTIR pattern of the non-crystalline aspirin illustrated in FIG. 4 provides relatively broad absorption bands. A comparison of the FTIR spectra of crystalline aspirin and the non-crystalline aspirin of the invention demonstrates that the two samples are the same chemical entity.

However, the broadening of the FTIR peaks of the sample analyzed in FIG. 4 is consistent with the non-crystalline form of the compound.

The difference in the crystal structure of prior art crystalline aspirin and the non-crystalline aspirin of the invention is also observed in polarized light microscopy (PLM) photomicrographs of the crystalline and non-crystalline forms. In polarized light microscopy, crystalline aspirin produces birefringence. Birefringence appears in anisotropic materials in which the molecules in the crystalline form are arranged in a highly ordered pattern that is absent in the non-crystalline form. As a result, polarized light microscopy photomicrographs of crystalline aspirin shows a high degree of birefringence that is not observed in purely non-crystalline aspirin, which lacks the ordered arrangement of molecules found in the crystalline form. Birefringence is clearly visible throughout a highly crystalline sample in a polarized light microscopy photomicrograph of the crystalline aspirin, exhibiting high order white interference colors.

In contrast, birefringence is not observed in polarized light microscopy photomicrographs of pure isotropic non-crystalline aspirin particles of the invention. The absence of birefringence is evidence of non-crystalline aspirin of the invention. As noted above, birefringence requires the ordered arrangement of molecules that is found in the crystalline form, but is not present in the non-crystalline form.

The non-crystalline aspirin of the invention is produced by exposing an aspirin solution to ultra-short pulses of laser light of different wavelengths from at least two sources at a relatively high pulse repetition rate, and evaporating the solvent. The pulses of laser light may be applied simultaneously or in alternating sequences.

The effective length of the laser pulses is preferably no greater than the picosecond range ($10^{-12}$ to $10^{-9}$ second), and may be in the femtosecond range ($10^{-15}$ to $10^{-12}$ second) or the sub-femtosecond range ($<10^{-15}$ second). One of the lasers preferably has an emission centered in the lower half of the visible spectrum, i.e., between about 400 and about 550 nm, preferably, in the near ultraviolet (UV) to blue range, more preferably, at a wavelength from about 400 to about 470 nm. The other laser preferably has an emission centered in the upper half of the visible spectrum, i.e., between about 550 and about 700 nm, preferably, in the red to near infrared (IR), more preferably at a wavelength of from about 620 to about 680 nm. Using two lasers having emissions centered at similar wavelengths, i.e., two short wavelength lasers, two long wavelength lasers, or two lasers with emissions centered near 550 nm, may be useful in some applications. However, good results have been obtained with one laser having a center wavelength of from about 400 to about 470 nm and a second laser having a center wavelength of from about 400 to about 470 nm.

Without being bound by theory, it is believed that the output bandwidth of the lasers is broadened by the effective short pulse length. This follows from the Uncertainty Principle. As a result, the short pulses of laser light are believed to provide photons that interact with multiple vibrational and/or electronic states of the aspirin to provide the non-crystalline form. As a result, lasers having an emission that corresponds to a specific absorption band of the aspirin are not required.

Preferably, the ultra-short laser pulses are produced by modifying the output of the lasers to generate sparse nodes of constructive interference of electromagnetic (EM) waves, as disclosed by U.S. Pat. Nos. 6,064,500 and 6,811,564 to Strachan, the disclosures of which are incorporated herein in their entirety by reference. As used herein, the term "Strachan Device" refers to a device of the type disclosed by Strachan in those patents. A Strachan Device, as defined in the '500 and '564 patents, and as used herein, comprises a first diffraction grating and a second diffraction grating and a refractive element positioned between the first and second diffraction gratings. When a laser beam, either continuous or pulsed, is passed through the first diffraction grating, the refractive element, and the second diffraction grating, at least a portion of the beam is substantially canceled by destructive interference. The interaction of light beams that pass through the Strachan Device results in destructive interference that substantially cancels the beams as they exit the Strachan Device. The refractive element allows the cancellation to occur over a small percentage of the laser source rather than at a single critical wavelength.

Relatively sparse zones of constructive interference occur between the high and low frequency passes of the cancellation element in selected directions from the aperture. The sparse nodes of constructive interference occur only where the output of the Strachan Device results in constructive interference at a distance from the device. The constructive interference only occurs over ultra-short time periods, and, thus, results in ultra-short pulses of light. The pulses are believed to have effective pulse lengths of no more than about $10^{-9}$ seconds.

With a Strachan Device, fractional changes in the wavelength of the laser or relative amplitudes of wavelengths in the laser cause rapid translation in the location of these nodes, as, for example, fractional changes in current in a laser diode and fluctuations in junction temperature causing variations in the laser center frequency. As a result, a continuous laser beam is transformed-into a string of extremely short duration pulses by the simple means of relatively small low frequency amplitude modulation. The amplitude modulation of diode lasers at a frequency of over 1 MHz is well within the skill of those skilled in the art. As a result, pulse lengths having a duration in the picosecond range are readily attainable, and femtosecond or sub-femtosecond pulses are attainable with a properly prepared Strachan Device and amplitude modulated diode laser.

For example, with a continuous diode laser, the pulse repetition frequency of the string of extremely short duration pulses is defined by the amplitude modulation frequency of the direct laser diode drive or the acousto-optic or electro-optic modulation device. The inherent current modulation of the direct laser drive method will result in more fluctuation in laser center frequency reducing the period of the coincident pulses while acousto-optic modulation provides a similar effect if the aperture of the modulated beam is greater than the diameter of the optimal modulation aperture of the crystal, as the outer radii will be less deeply modulated than the inner radii causing the effective aperture in the function to alter.

In the present method of producing the non-crystalline form of aspirin, a rapid, alternating sequence of ultra-short laser pulses from at least two different lasers are applied to the aspirin. As discussed above, it is believed that the output bandwidth of the lasers is broadened by the short pulse length. This follows from the Uncertainty Principle. As a result, the short pulses of laser light are believed to provide photons that interact with multiple vibrational and/or electronic states of the aspirin to provide the non-crystalline form. As a result, lasers having an emission that corresponds to a specific absorption band of the aspirin are not required, and, thus, the choice of lasers is not critical. Good results have been obtained using a laser that emits in the blue-violet band (preferably about 400 to about 470 nm) and a laser that emits in the red to near infrared wavelength band (preferably about 620 to about 680 nm).

Preferably, the preferred alternating sequence comprises sparse nodes of constructive interference of ultra short duration in the two wavelength regions that are produced using one or more Strachan Devices. Without being bound by theory, it is believed that the alternating sequence of ultrashort laser pulses interacts with the electronic and/or vibrational states of the aspirin, disrupting intermolecular interactions, and, thus, preventing crystal formation and/or disrupting the crystal structure.

The room temperature stable non-crystalline aspirin of the invention is preferably produced by the alternating application of amplitude modulated sparse constructive nodes from at least two different lasers that are passed through a Strachan Device, and applied to an aspirin solution in a solvent. Preferably, the alternating applications are repeated frequently.

Useful solvents are typically organic solvents in which aspirin is at least moderately soluble, that evaporate at about room temperature to about 130° C., and are nontoxic. Preferably, the aspirin is dissolved in an alcohol, and, more preferably, ethanol. Solvents are preferably anhydrous, and the most preferred solvent is anhydrous ethanol.

Preferably, the laser radiation is applied to the aspirin solution until the solvent is substantially evaporated. More preferably, the aspirin solution is heated during the application of the laser radiation and evaporation of the solvent. Most preferably, the laser radiation is first applied to the aspirin solution, where the solution is covered with a transparent cover that substantially prevents evaporation of the solvent. The transparent cover is then removed, and the application of laser radiation is continued as the solvent evaporates.

Preferably, the lasers comprise a laser that emits in the blue-violet wavelength and a laser that emits in the red-orange wavelength band. More preferably, the lasers preferably emit in the range of about 400 to about 470 nm and in the range of about 620 to about 680 nm, respectively. More than two lasers emitting at different wavelengths may be used with the invention. Good results have been obtained with a Strachan device and diode lasers that emit at 408 nm and 674 nm.

Although the process of the invention has been shown to provide non-crystalline aspirin in the presence of normal air, the process may also be performed in an inert atmosphere. The inert atmosphere may be provided using nitrogen, helium, argon, or other inert gas. For cost reasons, nitrogen is preferred. The use of the inert gas will eliminate any tendency of the aspirin to oxidize during the process.

The following non-limiting examples are merely illustrative of the preferred embodiments of the present invention, and are not to be construed as limiting the invention, the scope of which is defined by the appended claims.

As discussed above, non-crystalline aspirin is far from thermodynamic equilibrium at room temperature, and has always been found previously to be crystalline or to crystallize at temperatures above the glass transitions temperature, which is well below room temperature, up to the melt temperature. However, the repetitive application of laser radiation in accordance with the invention, converts aspirin to a predominant non-crystalline glass form that has been found to remain stable at room temperature for at least up to about a year.

EXAMPLE 1

A single sequence of 2.5 minutes each of long wavelength (red), 674 nm, followed by short wavelength (violet), 408 nm, amplitude modulated and structured laser light from a Strachan Device was applied to a solution of an aspirin in absolute ethanol. Each of the approximately 3 cm expanded beams was slowly rotated over the sample at a distance of 25 cm from the Strachan Device. An analysis of the treated aspirin with plane polarized light microscopy demonstrated the occasional production of a small fraction of tiny isotropic droplets of aspirin, generally less than one millimeter (1 mm) in size, that were stable at room temperature once the solvent had evaporated. Most of the droplets had a core of birefringent crystalline material and a halo of isotropic aspirin, though a few droplets were purely isotropic. The ability of the isotropic material to resist crystallization when abutting forming fronts of crystallized material demonstrates the stability of the non-crystalline aspirin of the invention produced through this method once desolvation has occurred.

EXAMPLE 2

The frequent, repeated sequenced application of laser radiation to produce stable non-crystalline glass aspirin resulted in the production of up to about 80 to about 90 percent or more of transparent glass non-crystalline aspirin. Droplets of pure glassy material of about 2 to 3 mm or more and lakes of glass aspirin dozens of millimeters wide have been found to be stable for up to about a year at room temperature.

As discussed above, a reference standard crystalline aspirin was analyzed by PXRD. The characteristic pattern of reflection peaks of the reference standard crystalline aspirin is illustrated in FIG. 1. The crystalline aspirin was also analyzed using Fourier transform infrared spectroscopy, as illustrated in FIG. 3. As the PXRD pattern of a compound in the non-crystalline state results in disappearance of characteristic reflection peaks, FTIR spectroscopy confirms compound identification, and provides further evidence of the non-crystalline state by showing a broadening of absorption bands that occurs in the non-crystalline compared to the crystalline state.

The highly non-crystalline glass state of aspirin was produced by repeated applications of cycles of sequences of long wavelength followed by short wavelength laser light modulated and structured by a Strachan Device. A 10 mg sample of a crystalline aspirin reference standard was dissolved in 450 mg of absolute ethanol by stirring at 9000 revolutions per minute (rpm) with a magnetic stirrer, while heating to 140° C. for 12.5 minutes in a stoppered Erlenmeyer flask. The solution was transferred into a 60 mm×15 mm glass Petri dish, covered with a glass lid. The Petri dish was heated to 100° C. on a hot plate.

The aspirin solution was treated with repeated cycles of laser radiation modified with a Strachan Device. The first cycle was the application of amplitude modulated diode laser light from a diode laser having a central wavelength of 674 nm. The second cycle was the application of amplitude modulated diode laser light from a diode laser having a central wavelength of 408 nm. The sample was rotated slowly through each of the approximately 3 cm expanded beams at a distance of 25 cm from the Strachan Device.

The 674 nm laser diode beam had a peak power of 4.80 mW without optics. After passing through a Thorlabs 5× beam expander and the Strachan Device the peak power was reduced by about 50 percent. Using the Strachan Device, the 674 nm beam was adjusted to the 80 percent phase cancellation level to obtain a 3 cm diameter beam of about 0.48 mW.

The 408 nm beam had a peak power of about 4.8 mW without added optical elements. After passing through a Thorlabs 5× beam expander and the Strachan Device the peak power was reduced by about 50 percent. Using the Strachan Device, the 408 nm beam was adjusted to the 80 percent phase cancellation level to obtain a 3 cm diameter beam of about 0.48 mW.

Both beams were electronically amplitude modulated at 6.25 Megahertz (MHz). As discussed above, without being bound by theory, it is believed that the output bandwidth of the lasers is broadened by the short pulse length produced by the Strachan Device, which follows from the Uncertainty Principle. This provides interaction of the photons in the laser light with multiple electronic and/or vibrational modes of the aspirin molecules.

The aspirin solution was treated in the covered glass Petri dish while on the hot plate for one minute with the 674 nm configuration, then for one minute with the 408 nm configuration as above. This was followed with another cycle of the amplitude modulated and structured 674 nm configuration, followed by the 408 nm laser configurations for one minute for each laser system. The third sequence of the 674 nm laser followed by the 408 nm laser treatment was for 2 minutes with each laser system.

After this cycle the glass cover was removed from the Petri dish to permit evaporation of the ethanol. For the duration of the laser treatments, spanning 5 more cycles, the aspirin in ethanol solution remained on the hot plate. The next cycle of 674 nm followed by 408 nm laser treatments was for 2 minutes with each laser system. The next 4 cycles of 674 nm followed by 408 nm laser treatments applied 2 minutes per cycle with the laser systems applied for one minute each per cycle. Upon completion of the last cycle of laser treatment the sample of laser treated aspirin was removed from the hot plate to continue the process of solvent evaporation at a room temperature of about 18° to 20° C. and a humidity of 35 percent.

At the end of the laser treatment, most of the solvent had already evaporated, resulting in a "lake" of clear transparent glass aspirin approximately 3 cm wide. A narrow rim of crystallization had formed around the outer margin of the lake in a band representing approximately 30 percent of the circumferential perimeter. Despite the formation of an active crystallization front, there was negligible extension of this front after completion of the cycles of the sequenced laser treatments.

Within an hour of the evaporative desolvation process following the laser treatment, the system stabilized with 80 percent or more of the mass of the sample cured to a clear non-crystalline glass rather than a crystalline form. Continued storage at a room temperature of about 18° to 22° C. and about 30 to 40 percent humidity resulted in no change in appearance of the sample during a period of over 6 months duration, with preservation of the wide expanse of transparent glass aspirin even adjacent to the rim of crystallization.

After the 6 months of storage, the laser treated aspirin was studied by PXRD. This pattern, shown in FIG. 2, demonstrates this material to be highly X-ray non-crystalline, in marked contrast to the highly crystalline pattern shown in FIG. 1 for the control crystalline aspirin. Compared to the high intensity reflection peaks seen for crystalline aspirin, for laser treated aspirin these peaks are essentially completely eliminated, indicating that at most only very short range ordering remains in the non-crystalline glass form produced. No crystallization has been observed following an additional six months of storage. Those observations demonstrate the stability of the non-crystalline form of aspirin produced with the method of the invention.

The X-ray non-crystalline aspirin sample was then scanned using Fourier transform infrared (FTIR) spectroscopy, as shown in FIG. 4. In comparison to the FTIR spectroscopy of aspirin reference crystalline material shown in FIG. 3, relatively broad absorption bands are evident in the X-ray non-crystalline samples of aspirin as compared with the more defined bands of the crystalline aspirin reference sample. Infrared spectra of crystalline materials typically exhibit sharper or better resolved absorption bands than the non-crystalline form because of the reduced freedom of movement of the molecules in a crystalline lattice. Some bands in an infrared spectrum may also be shifted somewhat because of changes in form between crystalline materials and the non-crystalline form of the same compound. Comparing the FTIR spectra of crystalline aspirin and laser treated aspirin, these compounds are clearly the same chemical entity. The broadening of the spectral peaks in laser treated aspirin is an additional feature consistent with the non-crystalline form of aspirin.

EXAMPLE 3

Subsequent tests with the protocol of Example 2 were repeated with the order of long and short wavelengths reversed, i.e., short wavelength followed by long wavelength cycled sequenced laser treatment. This protocol also produced up to 90 percent yields of room temperature stable non-crystalline glass aspirin, which remained stable at room temperature for over 23 months. The Petri dish containing such a sample of non-crystalline aspirin was placed on edge for a period of about six weeks. No flowing of the sample was observed.

COMPARATIVE EXAMPLE

Figure 5:
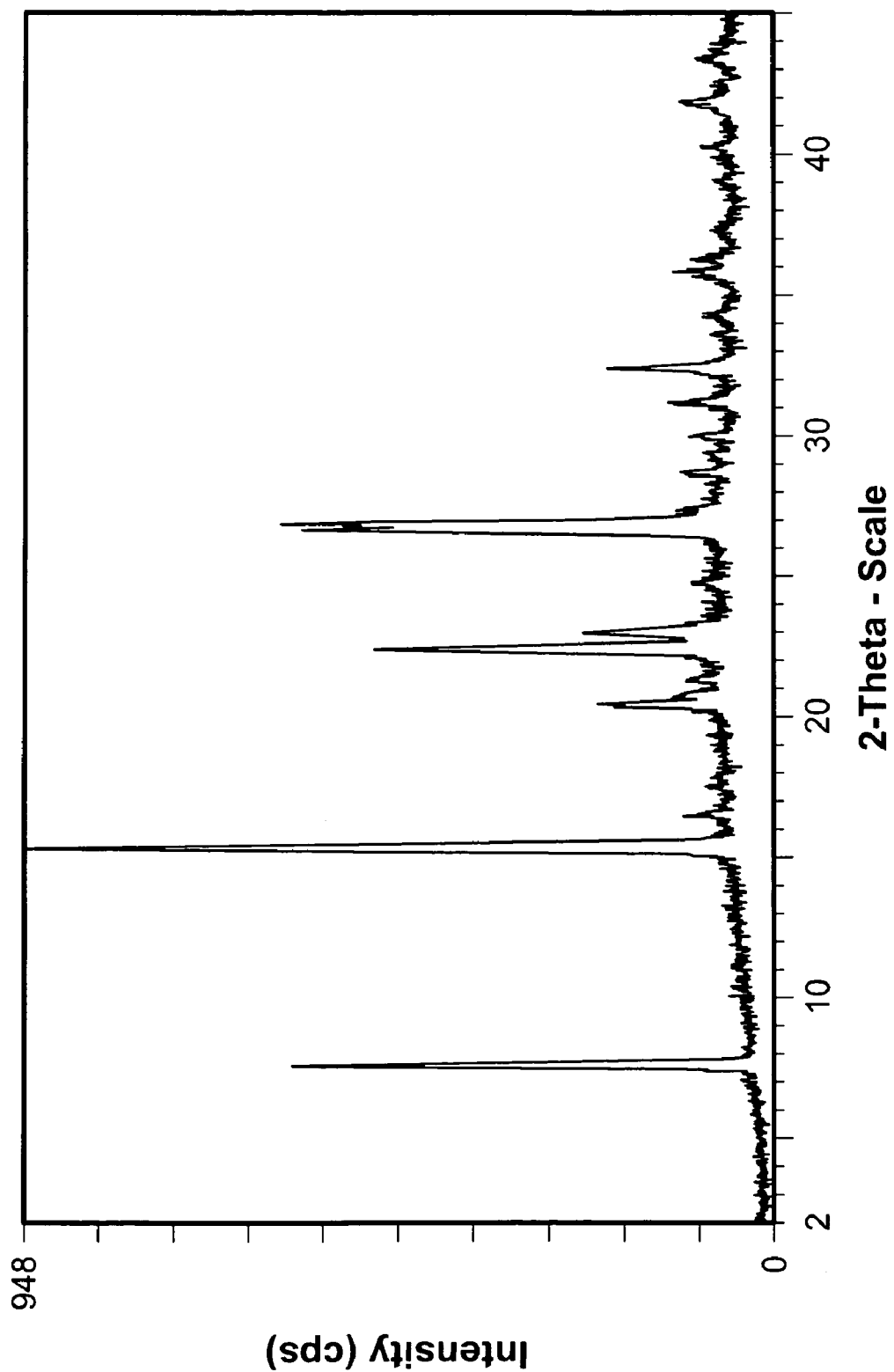
FIG. 5 illustrates the powder X-ray diffraction (PXRD) pattern of crystalline aspirin formed in the process similar to that of the invention, but without the application of laser radiation.
Figure 6:
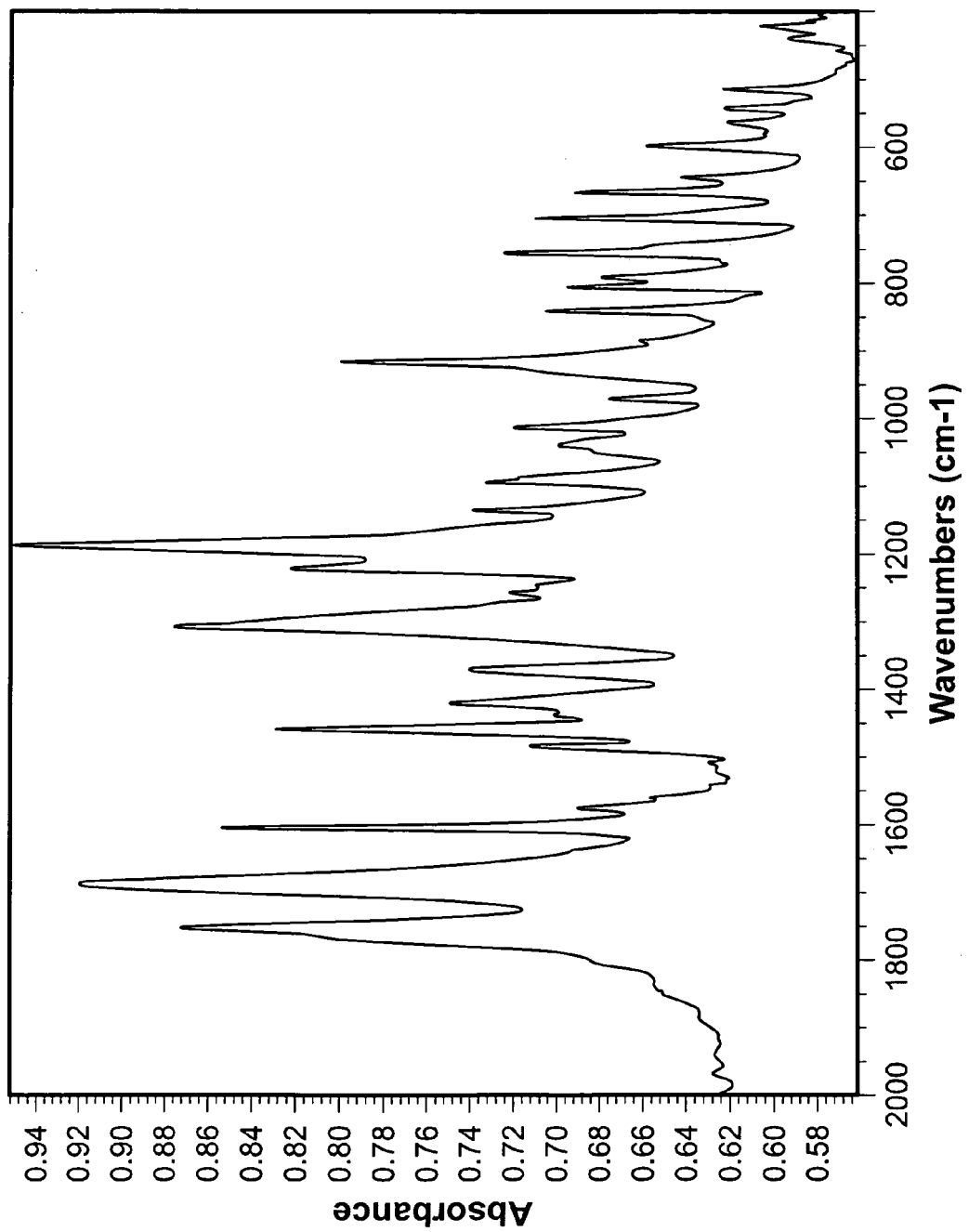
FIG. 6 illustrates an infrared spectroscopic pattern of the crystalline aspirin sample of FIG. 5.

The protocols of Example 2 and 3 were repeated with the exception that there was no application of laser radiation. The resulting material was visibly crystalline, which was confirmed by PXRD analysis. A PXRD pattern for crystalline aspirin obtained without the application of the laser radiation is illustrated in FIG. 5. The PXRD pattern of FIG. 5 has the same peaks as that of the control sample illustrated in FIG. 1. An FTIR analysis of the resulting crystalline aspirin was also performed. The resulting spectrum is illustrated in FIG. 6, and is substantially the same as that illustrated in FIG. 3. Those results clearly demonstrate that the non-crystalline aspirin is not an artifact of the experiment, but, instead, is a direct result of the application of the laser radiation in the process of the invention.

The stable non-crystalline glass aspirin of the invention retains the non-crystalline form during prolonged storage at room temperature. As a result, the use of the non-crystalline form is practical for clinical use or other applications for the first time. For example, as the non-crystalline form of a compound is believed to be more soluble than the crystalline form of the same compound, the non-crystalline aspirin should dissolve more rapidly and be more active at lower doses. In particular, this form offers the potential for a fast acting aspirin that relieves clinical symptoms more quickly at a lower dose with a reduced tendency to mucosal irritation.

To achieve large scale production of this form, microencapsulation permits generation and sealing of smaller particle sizes that are intrinsically more stable than larger particles composed of the non-crystalline aspirin. Microencapsulation will facilitate retaining stability during long term storage over a wider range of temperature and humidity. The non-crystal line aspirin of the invention may also enhance the practicality of rapidly absorbed mucosal or topical delivery systems. Microencapsulation techniques are well known in the art.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

What is claimed:

1. A process for the preparation of solid non-crystalline aspirin, comprising applying laser radiation from at least two different lasers to a solution of aspirin in a solvent, and evaporating the solvent, wherein the laser radiation has an effective average pulse length of no more than about $10^{-9}$ seconds, and the laser radiation from each laser is of a different wavelength.

2. A stable, solid non-crystalline aspirin produced by the process of claim 1, wherein there is substantially no crystallization in an entire sample of the stable, solid non-crystalline aspirin during storage for at least about 30 days at a temperature of from about 20° to about 30° C.

3. The stable, solid non-crystalline aspirin of claim 2, wherein there is substantially no crystallization in the entire sample of the stable, solid non-crystalline aspirin during storage for at least about six months at a temperature of from about 20° to about 30° C.

4. The stable, solid non-crystalline aspirin of claim 2, wherein the non-crystalline aspirin is microencapsulated.

5. The process of claim 1, wherein at least one of the lasers emits visible light.

6. The process of claim 1, wherein one laser emits radiation in the near UV to blue range, and one laser emits radiation in the red to near IR range.

7. The process of claim 1, wherein one laser emits radiation having a wavelength in the range of from about 400 to about 470 nm, and one laser emits radiation having a wavelength in the range of from about 620 to about 680 nm.

8. The process of claim 1, wherein the laser radiation is modified with a Strachan Device, the Strachan Device comprising a first diffraction grating, a second diffraction grating, and a refractive element positioned between the first and second diffraction gratings, wherein the Strachan Device cancels a portion of the laser radiation by destructive interference, and produces pulses of laser radiation by constructive interference.

9. The process of claim 8, wherein the lasers are diode lasers.

10. The process of claim 1, wherein the laser radiation has an effective average pulse length of no more than about $10^{-12}$ seconds.

11. The process of claim 1, wherein the laser radiation has an effective average pulse length of no more than about $10^{-15}$ seconds.

12. The process of claim 1, further comprising applying the laser pulses from at least two different lasers simultaneously.

13. The process of claim 1, further comprising applying laser pulses from at least two different lasers in alternating sequences.

14. The process of claim 1, wherein the solvent is an alcohol.

15. The process of claim 1, wherein the solvent is an absolute alcohol.

16. The process of claim 1, further comprising obtaining a solution of aspirin in a solvent;
placing the aspirin solution in a covered container;
applying the pulses of laser radiation pulses to the aspirin solution; and
evaporating at least a portion of the solvent while applying the laser pulses, thereby forming non-crystalline aspirin.

17. The process of claim 16, further comprising heating the aspirin solution during the application of the laser pulses.

18. The process of claim 17, further comprising heating the solution to a temperature of about 100° C.

19. The process of claim 16, further comprising applying the laser radiation to the aspirin solution until the evaporation of the solvent is completed.

20. The process of claim 19, further comprising cooling the aspirin to room temperature as the solvent evaporates.

21. The process of claim 16, further comprising preventing evaporation of solvent for a period of time after the application of laser pulses is initiated, and then evaporating solvent while the application of laser pulses is continued.

22. The process of claim 21, further comprising applying the laser radiation of the solution until the evaporation of the solvent is completed.

23. The process of claim 16, further comprising applying the laser pulses from at least two different lasers simultaneously.

24. The process of claim 16, further comprising applying laser pulses from at least two different lasers in alternating sequences.

25. The process of claim 16, wherein the laser pulses are laser emissions modified with a Strachan Device, the Strachan Device comprising a first diffraction grating, a second diffraction grating, and a refractive element positioned between the first and second diffraction gratings, wherein the Strachan Device cancels a portion of the laser radiation by destructive interference, and produces pulses of laser radiation by constructive interference.

26. A pharmaceutical composition, comprising the stable, solid non-crystalline aspirin of claim 2.

27. A stable, solid non-crystalline aspirin, having a PXRD pattern substantially as depicted in FIG. 2, wherein there is substantially no crystallization in an entire sample of the stable, solid non-crystalline aspirin during storage for at least about 30 days at a temperature of from about 20° to about 30° C.

28. A process for preparing solid non-crystalline aspirin, the process comprising:
passing laser radiation through a Strachan Device, the Strachan Device comprising a first diffraction grating and a second diffraction grating and a refractive element positioned between the first and second diffraction gratings, wherein the Strachan Device cancels a portion of the laser radiation by destructive interference, and produces pulses of laser radiation by constructive interference;
applying the laser radiation passed through the Strachan Device to a solution of aspirin in a solvent; and
evaporating the solvent.

29. The process of claim 28, wherein the pulses of laser radiation have an effective average pulse length of no more than about $10^{-9}$ seconds.

30. A stable, solid non-crystalline aspirin produced by the process of claim 28, wherein there is substantially no crystallization in an entire sample of the stable, solid non-crystalline aspirin during storage for at least about 30 days at a temperature of from about 20° to about 30° C.

31. The stable, solid non-crystalline aspirin of claim 30, wherein there is substantially no crystallization in the entire sample of the stable, solid non-crystalline aspirin during storage for at least about six months at a temperature of from about 20° to about 30° C.

32. The stable, solid non-crystalline aspirin of claim 30, wherein the non-crystalline aspirin is microencapsulated.

33. A pharmaceutical composition, comprising the stable, solid non-crystalline aspirin of claim 30.

* * * * *